US 8,596,058 B2

(12) United States Patent
Matsumoto et al.

(10) Patent No.: US 8,596,058 B2
(45) Date of Patent: Dec. 3, 2013

(54) HYDRAULIC SYSTEM AND UNIVERSAL TESTING MACHINE

(75) Inventors: Sigeru Matsumoto, Musashino (JP);
Hiroshi Miyashita, Tama (JP);
Kazuyoshi Tashiro, Sagamihara (JP);
Kazuhiro Murauchi, Hachioji (JP);
Mitsuo Kakuta, Sagamihara (JP)

(73) Assignee: Kokusai Keisokuki Kabushiki Kaisha, Tokyo (JP)

( * ) Notice: Subject to any disclaimer, the term of this patent is extended or adjusted under 35 U.S.C. 154(b) by 72 days.

(21) Appl. No.: 13/290,481

(22) Filed: Nov. 7, 2011

(65) Prior Publication Data

US 2012/0048029 A1    Mar. 1, 2012

Related U.S. Application Data

(63) Continuation-in-part of application No. PCT/JP2010/052998, filed on Feb. 25, 2010.

(30) Foreign Application Priority Data

May 22, 2009    (JP) ................................. 2009-124171

(51) Int. Cl.
*F16D 31/02*    (2006.01)
(52) U.S. Cl.
USPC ................................. 60/468; 60/295; 73/861
(58) Field of Classification Search
USPC ................................. 73/861; 60/295, 468, 421
See application file for complete search history.

(56) References Cited

U.S. PATENT DOCUMENTS

| | | | | |
|---|---|---|---|---|
| 5,115,835 A | * | 5/1992 | Ueno | 137/596.13 |
| 7,069,723 B2 | * | 7/2006 | Yamamoto et al. | 60/468 |
| 7,412,826 B2 | * | 8/2008 | Horii | 60/421 |
| 2007/0169563 A1 | | 7/2007 | Hohjo et al. | |

FOREIGN PATENT DOCUMENTS

| | | |
|---|---|---|
| JP | SHO 61-248450 | 11/1986 |
| JP | HEI 6-337002 | 12/1994 |
| JP | HEI 9-184591 | 7/1997 |
| JP | HEI 10-60953 | 3/1998 |
| JP | 2001-66233 | 3/2001 |
| JP | 2001-159593 | 6/2001 |
| JP | 2007-198783 | 8/2007 |

OTHER PUBLICATIONS

Korean Office Action issued in KR 10-2011-7028327 on Jun. 10, 2013.

* cited by examiner

*Primary Examiner* — Jewel V Thompson
(74) *Attorney, Agent, or Firm* — McCarter & English, LLP

(57) ABSTRACT

There is provided a hydraulic system, including an oil tank storing operating oil, a hydraulic actuator, and a hydraulic pump which draws the operating oil from the oil tank and supplies the operating oil to the hydraulic actuator. The hydraulic system is provided with an operating oil separating unit which is located at a midway point of a main tube sending the operating oil from the hydraulic pump to the hydraulic actuator and which separates a part of the operating oil supplied from the hydraulic pump to return the part of the operating oil to the oil tank. A universal testing machine including the hydraulic system is also provided.

20 Claims, 6 Drawing Sheets

HYDRAULIC SYSTEM AND UNIVERSAL TESTING MACHINE

This is a Continuation-in-Part of International Application No. PCT/JP2010/052998 filed Feb. 25, 2010, which claims priority from Japanese Patent Application No. 2009-124171 filed May 22, 2009. The entire disclosure of the prior application is hereby incorporated by reference herein its entirety.

TECHNICAL FIELD

The present invention relates a hydraulic system which generates a hydraulic pressure by driving a hydraulic pump with an electric motor, and specifically to a hydraulic system which controls a flow amount of operating oil by controlling the number of revolutions of the electric motor. Furthermore, the present invention relates to a universal testing machine provided with such a hydraulic system.

BACKGROUND

Universal testing machines (material testing machines) are widely used to measure mechanical properties of materials and components. The universal testing machine applies a stress, such as a tensile stress, a compressive stress or a bending stress, to a test piece, and measures the mechanical property, such as a breaking strength, an elastic coefficient and hardness based on behavior of the test piece. A typical universal testing machine includes a moving plate and a fixed plate, and applies load to the test piece by fixing one end of the test piece to the moving plate and fixing the other end of the test piece to the fixed plate (or by sandwiching the test piece between the moving plate and the fixed plate) and then moving the moving plate with respect to the fixed plate.

As an example of a mechanism for driving the moving plate of the universal testing machine, Japanese Patent Provisional Publication No. 2001-159593A describes a hydraulic mechanism. The hydraulic system mechanism controls a flow amount of operating oil to be supplied to a hydraulic cylinder by adjusting a discharge amount of a hydraulic pump driven by a servo motor, not by adjustment of opening of a servo valve. In the hydraulic mechanism, the flow amount of the operating oil to be supplied to the hydraulic cylinder is precisely controlled by controlling the number of revolutions of the servo motor which drives the hydraulic pump.

SUMMARY

The universal testing machine is used principally for a static test for measuring a response property of a test piece with respect to static load. Practically, the test is performed by applying a sufficiently low distortion rate to the test piece so as to continuously measure the static property within a range from no load to breaking load. Therefore, it is necessary to move the moving plate at a low speed during the test.

In the universal testing machine which uses a conventional hydraulic actuator of a type driving a hydraulic pump with a servo motor, it is necessary to suppress the flow amount of the operating oil supplied from the hydraulic pump to a low level by lowering the rotation speed of the hydraulic pump. However, if the rotation speed of the hydraulic pump decreases, a pulsating flow is caused in the operating oil. Therefore, it was impossible to supply the operating oil in a stable flow amount to the hydraulic cylinder. For this reason, in the conventional universal testing machine, the moving speed of the moving plate is lowered by increasing the diameter of the hydraulic cylinder. However, there is a problem that, if the diameter of the hydraulic cylinder is increased, the entire size of the universal testing machine increases.

The present invention is made in consideration of the above described circumstances. That is, the present invention is advantageous in that it provides a hydraulic system capable of precisely driving an actuator at a low speed in a low level of fluctuation of the oil pressure during a state of a low flow amount, and provides a compact universal testing machine including such a hydraulic system.

According to an aspect of the invention, there is provided an hydraulic system, which is provided with an oil tank storing operating oil, a main hydraulic actuator, a second hydraulic actuator which operates at a hydraulic pressure lower than or equal to a predetermined pressure, a hydraulic pump which draws the operating oil from the oil tank and supplies the operating oil to the main and second hydraulic actuators, a main tube which sends the operating oil from the hydraulic pump to the main hydraulic actuator, a second tube which sends the operating oil to the second hydraulic actuator, and an operating oil separating unit which is located at a midway point of the main tube and which separates a part of the operating oil supplied from the hydraulic pump to return the part of the operating oil to the oil tank. In this configuration, the operating oil separating unit includes a branch tube which branches out from the main tube, undo reducing valve having an inlet port connected to the branch tube, an outlet port connected to the second tube, and a relief port connected to the oil tank. The reducing valve reduces a pressure of the outlet port to be lower than or equal to a predetermined pressure by separating the part of the operating oil introduced from the inlet port to proceed from the relief port to the oil tank. A flow amount of the operating oil separated by the reducing valve is set to a value which the hydraulic pump should maintain to reduce pulsation to be lower than or equal to a desired level.

The hydraulic system configured as described above returns a predetermined amount of operating oil from the operating oil separating unit to the oil tank even when the main hydraulic actuator is driven at a low speed. Therefore, it is possible to maintain the discharge amount of the hydraulic pump at an amount by which pulsation can be suppressed to be lower than or equal to a desired level. Accordingly, even when the main hydraulic actuator is driven at a low speed, the hydraulic system does not cause vibration in the main hydraulic actuator. Therefore, the hydraulic system can be applied to, thr example, a purpose which requires low speed driving and a low level of vibration, such as a universal testing machine.

In at least one aspect, a discharge pressure of the hydraulic pump may be supplied to the main hydraulic actuator without being substantially reduced.

In at least one aspect, the main hydraulic actuator may be connected to the hydraulic pump without intervention by a flow control valve for controlling continuously a flow amount.

In at least one aspect, the main hydraulic actuator may be connected to the hydraulic pump without intervention by a throttle valve.

In at least one aspect, the hydraulic system may further include a motor which drives the hydraulic pump.

In at least one aspect, the motor may be a servo motor.

In at least one aspect, the hydraulic pump may be a piston pump.

According to another aspect of the invention, a universal testing machine including one of the above described hydraulic systems is provided.

According to another aspect of the invention, there is provided a universal testing machine, which includes a fixed plate, a moving plate capable of moving with respect to the fixed plate, and a hydraulic system which moves the moving plate so as to apply a static load to a test piece held between the fixed plate and the moving plate. In this configuration, the hydraulic system includes an oil tank storing operating oil, a main hydraulic cylinder having a piston and a sleeve, one of which is fixed to the moving plate, the main hydraulic cylinder being able to operate at a hydraulic pressure higher than a predetermined pressure, a hydraulic pump which draws the operating oil from the oil tank and supplies the operating oil to the main hydraulic cylinder, a servo motor which drives the hydraulic pump, an operating oil separating unit which is located between the hydraulic pump and the main hydraulic cylinder and which separates a part of the operating oil supplied from the hydraulic pump to return the part of the operating oil to the oil tank, and a chuck unit having a holding arm which holds the test piece and a chuck hydraulic cylinder which drives the holding arm by the operating oil supplied from the hydraulic pump. The operating oil separating unit is a reducing valve having an inlet port connected to the hydraulic pump, an outlet port connected to the chuck cylinder, and a relief port connected to the oil tank. The reducing valve reduces a pressure of the outlet port actuating the chuck hydraulic cylinder to be lower than or equal to a predetermined pressure by separating the part of the operating oil introduced from the inlet port to proceed from the relief port to the oil tank. A flow amount of the operating oil separated by the reducing valve is set to a value which the hydraulic pump should maintain to reduce pulsation to be lower than or equal to a desired level.

The hydraulic system configured as described above returns a predetermined amount of operating oil from the operating oil separating unit to the oil tank even when the main hydraulic actuator is driven at a low speed. Therefore, it is possible to maintain the discharge amount of the hydraulic pump at an amount by which pulsation can be suppressed to be lower than or equal to a desired level. Accordingly, even when the main hydraulic actuator is driven at a low speed, the hydraulic system does not cause vibration in the main hydraulic actuator.

In at least one aspect, the chuck unit may hold the test piece when the operating oil is supplied to one of hydraulic chambers of the chuck hydraulic cylinder and a piston is moved. The universal testing machine may further include a check valve which is located between the one of the hydraulic chambers of the chuck hydraulic cylinder and the hydraulic pump and which prevents back-flow of the operating oil from the one of the hydraulic chambers to the hydraulic pump while the test piece is held.

In at least one aspect, the universal testing machine may further include a switch valve which is located between the hydraulic pump and the chuck hydraulic cylinder and which switches between a state of sending the operating oil supplied from the hydraulic pump to the one of the hydraulic chambers and a state of sending the operating oil supplied from the hydraulic pump to the other of the other hydraulic chambers. In this case, the chuck unit releases a holding state of the test piece when the operating oil is supplied, to the other of the hydraulic chambers of the chuck hydraulic cylinder and the piston is moved. The check valve is a pilot check valve whose pilot port is connected to the other of the hydraulic chambers, and when the operating oil is supplied to the other of the hydraulic chambers, the pilot check valve opens and the operating oil is discharged from the one of the hydraulic chambers.

In at least one aspect, the universal testing machine may further include an accumulator arranged between the check valve and the one of the hydraulic chambers.

According to another aspect of the invention, there is provided a hydraulic system, which includes an oil tank storing operating oil, a first actuator, a hydraulic pump which draws the operating oil from the oil tank and supplies the oil tank to the first hydraulic actuator, a main tube which sends the operating oil from the hydraulic pump to the first actuator, and an operating oil separating unit which is located at a midway point of the main tube and which separates a part of the operating oil supplied from the hydraulic pump to return the part of the operating oil to the oil tank. In this configuration, the hydraulic pump comprises a servo motor, and is configured to be able to control a discharge amount of the operating oil by controlling a rotation speed of the servo motor. A flow amount of the operating oil separated by the operating oil separating unit is set to a value which the hydraulic pump should maintain to reduce pulsation to be lower than or equal to a desired level.

The hydraulic system configured as described above returns a predetermined amount of operating oil from the operating oil separating unit to the oil tank even when the main hydraulic actuator is driven at a low speed. Therefore, it is possible to maintain the discharge amount of the hydraulic pump at an amount by which pulsation can be suppressed to be lower than or equal to a desired level. Accordingly, even when the main hydraulic actuator is driven at a low speed, the hydraulic system does not cause vibration in the main hydraulic actuator. Therefore, the hydraulic system can be applied to, for example, a purpose which requires low speed driving and a low level of vibration, such as a universal testing machine.

In at least one aspect, the servo motor may be controlled to rotate at a rotation speed larger than or equal to a predetermined rotation speed so as to secure a certain flow amount of the operating oil required to suppress the pulsation to be lower than or equal to the desired level.

In at least one aspect, a flow amount of the operating oil separated by the he operating oil separating unit may be set such that a flow amount of the operating oil supplied to the first hydraulic actuator reduces and thereby a moving speed of a moving plate of the first hydraulic actuator becomes a speed required for a static load test.

In at least one aspect, the moving speed of the moving plate of the first hydraulic actuator may be lower than or equal to 0.1 mm/s.

According to another aspect of the invention, there is provided a universal testing machine, which includes a fixed plate, a moving plate capable of moving with respect to the fixed plate, and a hydraulic system which moves the moving plate so as to apply a static load to a test piece held between the fixed plate and the moving plate. The hydraulic system includes an oil tank storing operating oil, a main hydraulic cylinder having a piston and a sleeve, one of which is fixed to the moving plate, the main hydraulic cylinder being able to operate at a hydraulic pressure higher than a predetermined pressure, a hydraulic pump which draws the operating oil from the oil tank and supplies the operating oil to the main hydraulic cylinder, and an operating oil separating unit which is located between the hydraulic pump and the main hydraulic cylinder and which separates a part of the operating oil supplied from the hydraulic pump to return the part of the operating oil to the oil tank. In this configuration, the hydraulic pump includes a servo motor, and is configured to be able to control a discharge amount of the operating oil by controlling a rotation speed of the servo motor. A flow amount of the operating oil separated by the operating oil separating unit is set to a value which the hydraulic pump should maintain to reduce pulsation to be lower than or equal to a desired level.

The hydraulic system configured as described above returns a predetermined amount of operating oil from the operating oil separating unit to the oil tank even when the main hydraulic actuator is driven at a low speed. Therefore, it is possible to maintain the discharge amount of the hydraulic pump at an amount by which pulsation can be suppressed to be lower than or equal to a desired level. Accordingly, even when the main hydraulic actuator is driven at a low speed, the hydraulic system does not cause vibration in the main hydraulic actuator.

In at least one aspect, the servo motor may be controlled to rotate at a rotation speed larger than or equal to a predetermined rotation speed so as to secure a certain flow amount of the operating oil required to suppress the pulsation to be lower than or equal to the desired level.

In at least one aspect, a flow amount of the operating oil separated by the he operating oil separating unit may be set such that a flow amount of the operating oil supplied to the first hydraulic actuator reduces and thereby a moving speed of a moving plate of the first hydraulic actuator becomes a speed required for a static load test.

In at least one aspect, the moving speed of the moving plate of the first hydraulic actuator may be lower than or equal to 0.1 mm/s.

DETAILED DESCRIPTION OF EMBODIMENTS

Figure 1:
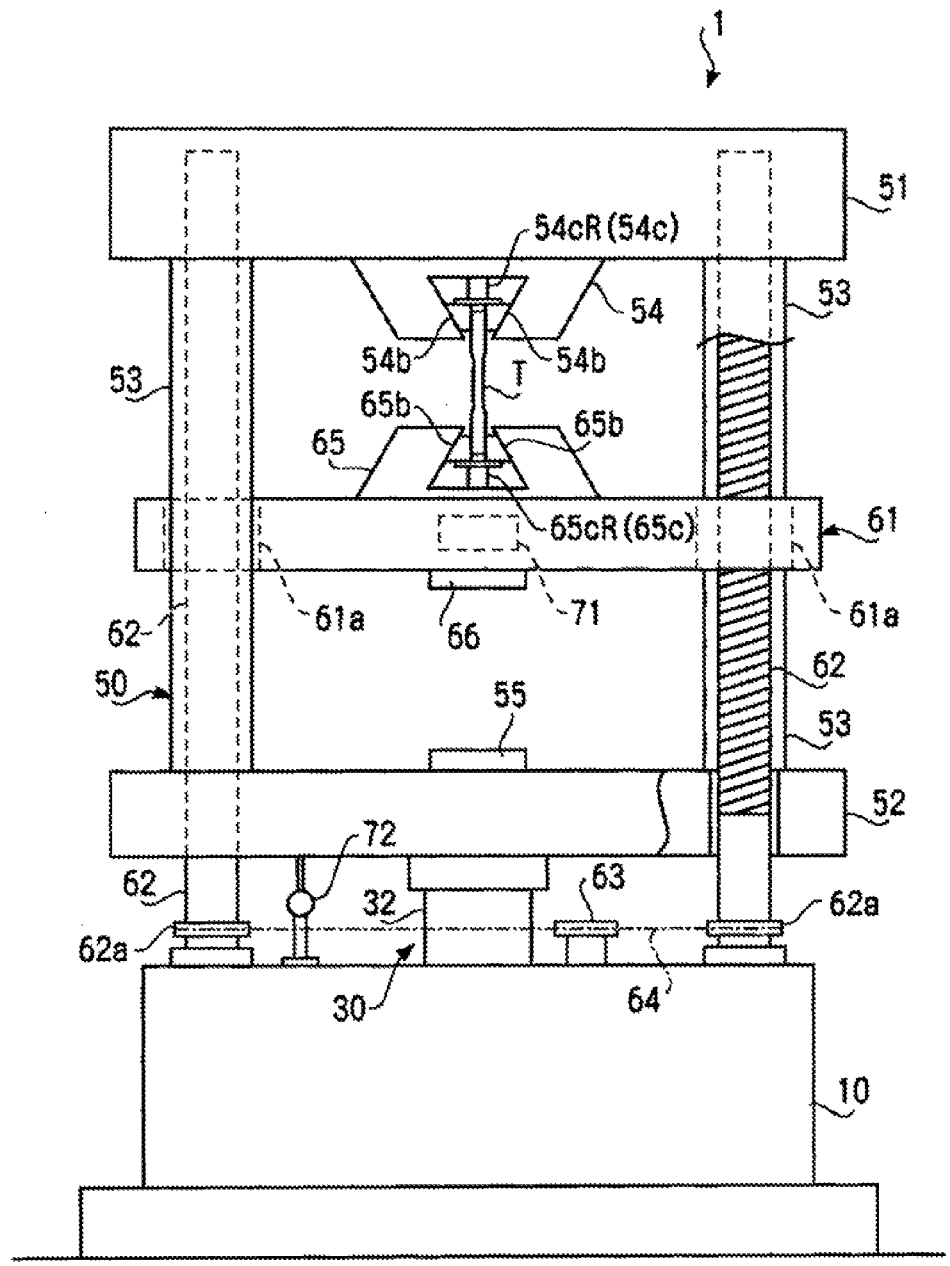
FIG. 1 is a front view generally illustrating a universal testing machine according to an embodiment of the invention during a tensile test.

In the following, detailed explanation of an embodiment of the present invention is made with reference to the accompanying drawings. FIG. 1 is a general front view of a universal testing machine 1 according to the embodiment of the invention. As shown in FIG. 1, the universal testing machine 1 includes a base frame 10, a moving plate 50 and a fixed plate 61. The universal testing machine 1 also includes a control and measurement unit 70 which is explained later. The moving plate 50 includes a top plate 51 and a bottom plate 52 which are arrange in a vertical direction, with each plate face being horizontally oriented. The top plate 51 and the bottom plate 52 are connected by four joint shafts 53 arranged to extend in the vertical direction (only three joint shafts are illustrated). Thus, the top plate 51 and the bottom plate 52 are able to move together.

At a central portion of the base frame 10, a main cylinder unit 30 is provided. The main cylinder unit 30 is a hydraulic cylinder configured to drive a piston 32 to linearly reciprocate by the hydraulic pressure. The piston 32 is fixed to a lower surface of the bottom plate 52. Therefore, by driving the piston 32 of the main cylinder unit 30, it is possible to move the entire moving plate 50 including the top plate 51 and the bottom plate 52 in the vertical direction.

To an upper surface of the base frame 10, lower ends of a pair of ball screws 62 extending in the vertical direction are fixed. Near a lower end of each ball screw 62, a sprocket 62a is attached to each ball screw 62. An endless chain 62 is wound around the sprockets 62a, and therefore the pair of ball screws 62 can be rotated by rotating the endless chain 64. In order to prevent the endless chain 64 and the main cylinder unit 30 to interfere with each other, at least two auxiliary sprockets 63 (only one auxiliary sprocket is illustrated in the drawing) are provided on the base frame 10, and a path of the endless chain 64 is broadened by the auxiliary sprockets 63 in a direction perpendicular to the paper face of FIG. 1 (in a depth direction).

A motor (not shown) for rotating the sprocket 63 is connected to one of the auxiliary sprockets 63. By rotating the auxiliary sprocket 63 with the motor, the torque propagates to the sprocket 62a via the endless chain 64, thereby rotating the ball screws 62. That is, it is possible to rotate the ball screws 62 by the motor connected to one of the auxiliary sprockets 63.

In the fixed plate 61, a pair of ball nuts 61a respectively engaging with the pair of ball screws 62 is buried. Since the fixed plate 61 engages with the two ball screws 62 via the ball nuts 61a, the rotational movement of the fixed plate 61 around one of the ball screws 62 is blocked by engagement between the other ball screws 62 and the ball nuts 61a. Therefore, the moving direction of the fixed plate 61 is restricted to the vertical direction. Accordingly, by rotating the ball screws 62 by the motor, it is possible to move the fixed plate 61 in the vertical direction. In accordance with the size of the test piece, the fixed plate 61 is driven in the vertical direction in order to adjust an initial interval between the fixed plate 61 and the moving plate 50 (the top plate 51 and the bottom plate 52).

On the lower surface of the top plate 51 and the upper surface fixed plate 61, chucking devices 54 and 65 are attached, respectively. The chucking devices 54 and 65 respectively hold an upper end and a lower end of a tensile test piece T. The chucking devices 54 and 65 are able to apply a tensile load to the tensile test pieces T by driving the main cylinder unit 30 and thereby moving upward the moving plate 50.

Figure 2:
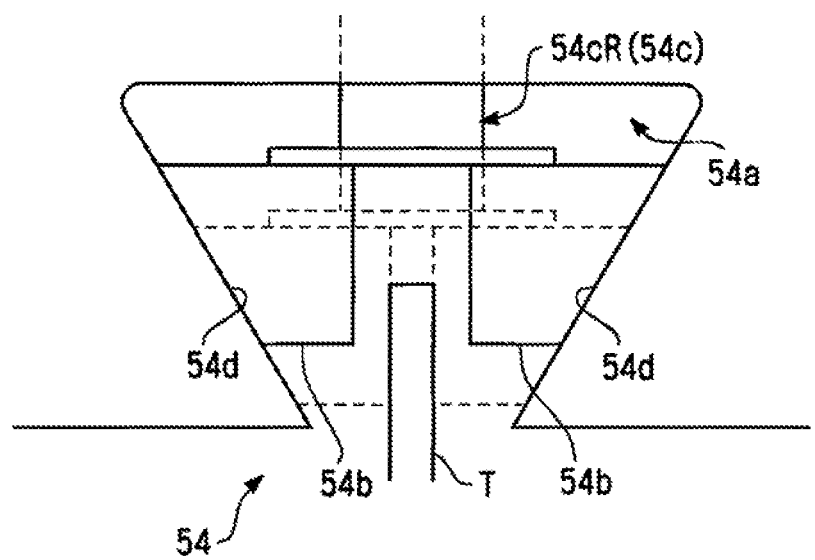
FIG. 2 is a front view generally illustrating, a chuck device of the universal testing machine according to the embodiment of the invention.

Next, structures of the chucking devices 54 and 65 are explained. FIG. 2 is a general front view of the chuck device 54 according to the embodiment. The chuck device 54 includes a recessed part 54a in which a pair of holding arms 54b and 54b is accommodated, and a chuck cylinder 54c which moves the holding arms 54b in the vertical direction.

As shown in FIG. 2, left and right end faces of the recessed part 54a are formed as slanting surfaces 54d formed to become closer to each other on a lower side. A side of the holding arm 54b facing the slanting surface 54d is also formed as a slanting surface parallel with the slanting surface 54d. The holding arms 54b are supported in the recessed part 54a to be slidable along the slanting surfaces 54d. A piston rod 54cR of the chuck cylinder 54c contacts upper edges of the holding arms 54b. By lowering the piston rod 54cR while driving the chuck cylinder 54c, it is possible to press down the holding arms 54b.

Furthermore, the holding arms 54h are pressed upward by a spring (not shown). Therefore, in a state where the piston rod 54cR is retracted on an upper side (a solid line part in FIG. 2), the holding arms 54b are situated to be away from each other.

When the piston rod 54 is lowered by driving the chuck cylinder 54c, the holding arms 54b are brought to the state o being close to each other, and the tensile test piece T is held between the pair of holding arms 54b.

As described above, the chuck device 54 according to the embodiment is configured such that the holding arms 54b slide along the slanting surfaces 54d. Therefore, in a state where the tensile load is applied to the tensile test piece T, the holding arms 54h are drawn toward the lower side by a frictional force with the tensile test piece T (i.e., in a direction in which the holding arms 54b become closer to each other), and thereby the holding force by which the holding arms 54b hold the tensile test piece 54b increases. Consequently, during the tensile test, the test piece is prevented from being removed from the chuck device 54.

It should be noted that the chuck device 65 has the same structure as that of the chuck device 54, and is configured to move holding arms 65b (see FIG. 1) by driving a piston rod 65cR of a chuck cylinder 65c. Therefore, detailed explanation of the chuck device 65 is omitted.

Figure 3:
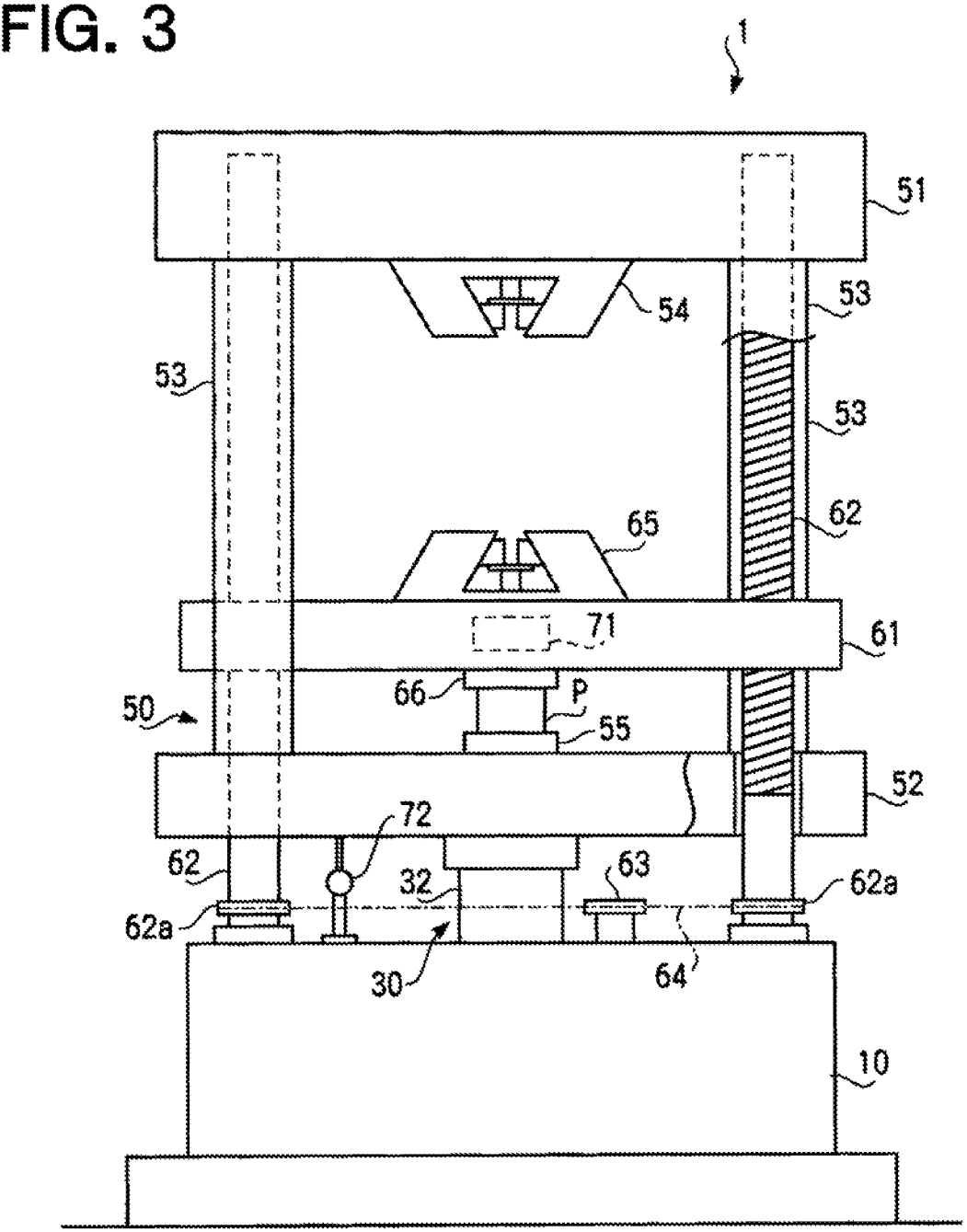
FIG. 3 is a front view generally illustrating the universal testing, machine according to the embodiment of the invention during a compression test.

In the universal testing machine 1 according to the embodiment, pressing jigs 66 and 55 are provided on the lower surface of the fixed plate 61 and the upper surface of the bottom plate 52, respectively. As shown in FIG. 3, the pressing jigs 66 and 55 are used to sandwich a compression test piece P therebetween from the upper and lower sides and thereby to apply a compressive load to the compression test piece P. That is, when the moving plate 50 is moved upward in a state where the pressing jigs 66 and 55 sandwich the compression test pieces P from the upper and lower sides, the compressive load is applied to the compression test piece P between the bottom plate 52 and the fixed plate 61.

As shown in FIGS. 1 and 3, the fixed plate 61 is provided with a load cell 71 for measuring the load applied to the fixed plate 61 (i.e., the tensile load applied to the tensile test piece T or the compressive load applied to the compression test piece P). Furthermore, the base frame 10 is provided with a displacement sensor 72 (e.g., a dial gauge including a rotary encoder) for measuring the distance between the base frame 10 and the bottom plate 52. A controller 75 (described later) of the universal testing machine 1 is able to calculate the stress applied to the testing piece based on the load measured by the load cell 71 and a section area of the test piece. Furthermore, the controller 75 is able to calculate distortion of the test piece based on the measurement result by the displacement sensor 72 and a natural length of the test piece.

Figure 4:
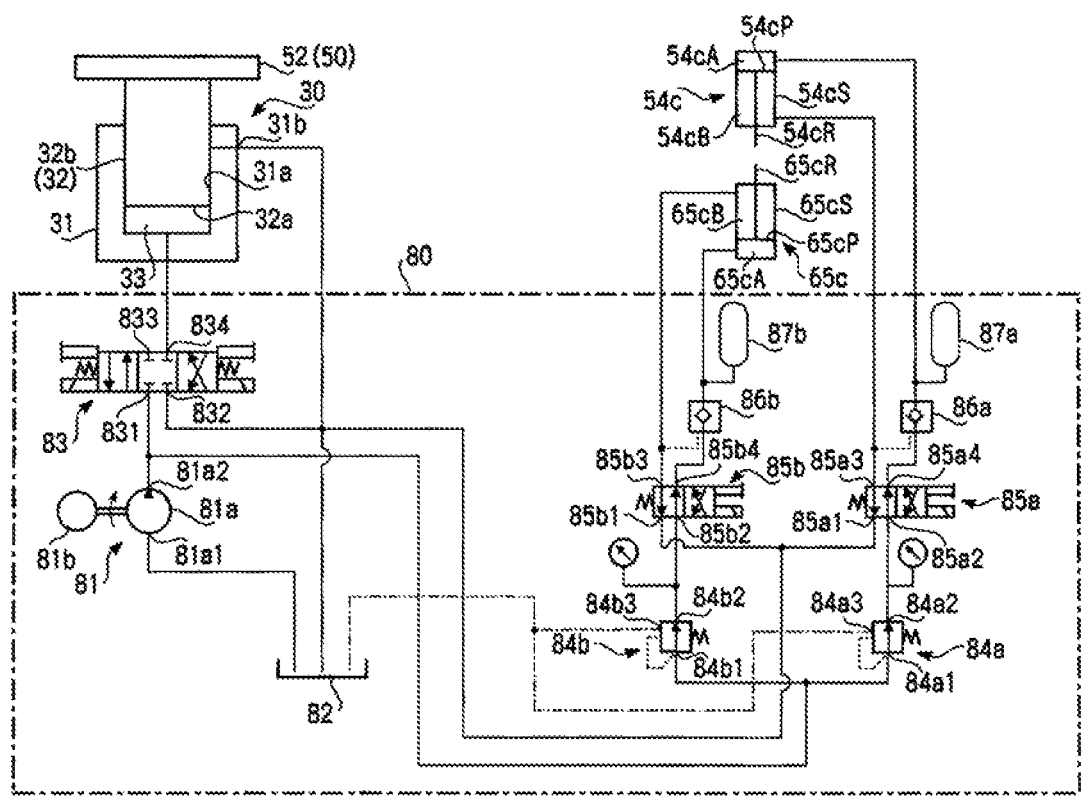
FIG. 4 is a diagram generally illustrating a hydraulic circuit of a hydraulic control system according to the embodiment of the invention.

Next, a hydraulic control system 80 according to the embodiment of the invention is explained. FIG. 4 is a block diagram generally illustrating a driving mechanism of the universal testing machine 1 including the hydraulic control system 80, the main cylinder unit 30 and the chuck cylinders 54c and 65c.

As shown in FIG. 4, the hydraulic control system 80 according to the embodiment of the invention includes an oil tank 82 storing the operating oil, and a pump unit 81 for drawing the operating oil from the oil tank 82 and supplying the operating oil to the main cylinder unit 30 and the chuck cylinders 54c and 65c.

The pump unit 81 includes a piston pump 81a for sucking the operating oil from an suction port 81a1 and discharging the operating oil from a discharge port 81a2, and a servo motor 81b for driving the piston pump 81a. The servo motor 81b is a motor whose rotation speed can be precisely controlled. By controlling the rotation speed of the servo motor 81b, it is possible to precisely adjust the discharge amount of the operating oil by the piston pump 81a.

The main cylinder unit 30 includes a sleeve 31 which accommodates the piston 32 to be slidable therein. By supplying the operating oil to an operating oil chamber 33 formed between a top face 32a of the piston 32 and the sleeve 31, it is possible to push up the piston 32.

Between the discharge port 81a2 of the piston pump 81a and the main cylinder unit 30, a first electromagnetic valve 83 is provided. The first electromagnetic valve 83 has a first port 831, a second port 832, a third port 833 and a fourth port 834. The first electromagnetic valve 83 is configured such that a first state where the all the ports are closed under control of the external controller 75, a second state where the first port 831 and the third port 833 are connected and the second port 832 and the fourth port 834 are connected and a third state where the first port 831 and the fourth port 834 are connected and the second port 832 and the third port 833 are connected can be switched.

The first port 831, the second port 832 and the fourth port 834 of the first electromagnetic valve 83 are connected respectively to the discharge port 81a2, the oil tank 82 and the main cylinder unit 30. The third port 833 is closed.

If the first electromagnetic valve 83 is switched to the third state while the pump unit 81 is drawing the operating oil, the operating oil is supplied to the operating oil chamber 33 of the main cylinder unit 30, and the piston 32 and the moving plate 50 fixed to the piston 32 are pushed up. In the hydraulic control system 80 according to the embodiment of the invention, the main cylinder unit 30 is connected to the discharge port 81a2 of the piston pump 81.a without intervention by a throttle valve (a flow amount restriction valve). That is, the moving rate of the piston 32 can be adjusted by controlling the pressure and the flow amount of the operating oil supplied by the pump unit 81 (i.e., by controlling the rotation speed of the servo motor 81b).

When the state of the first electromagnetic valve 83 is switched to the first state, the operating oil chamber 33 is separated from a hydraulic circuit, and the position of the piston 32 is fixed.

When the state of the first electromagnetic valve 83 is switched to the second state, the operating oil chamber 33 is connected to the oil tank 82, the operating oil in the operating oil chamber 33 returns to the oil tank 82, and the piston 32 and the moving plate 50 is lowered.

In a state where the inner pressure of the operating chamber 33 is high, there is a possibility that the operating oil leaks through a gap between an inner circumferential surface 31a of the sleeve 31 and an outer circumferential surface 32b of the piston 32. In the sleeve 31, a recovering port 31b for recovering the operating oil leaked from the gap is provided. The recovering port 31b is connected to the oil tank 82, and the leaked operating oil is returned to the oil tank 82.

Next, driving of the chuck cylinders 54c and 65c is explained.

As shown in FIG. 4, the chuck cylinder 54c is a double action hydraulic cylinder including a sleeve 54cS and a piston 54cP provided in the sleeve 54cS to be slidable. An inner space of the sleeve 54cS is divided by the piston 54cP into a head side hydraulic chamber 54cA and a rod side hydraulic chamber 54cB. The divided chambers are connected respectively to the hydraulic circuit. By supplying the operating oil to the head side hydraulic chamber 54cA and by discharging the operating oil from the rod side hydraulic chamber 54cB, the piston rod 54cR is lowered, and the holding arms 54b (see FIG. 2) hold the tensile test piece T. By discharging the operating oil from the head side hydraulic chamber 54cA and by supplying the operating oil to the rod side hydraulic chamber 54cB, the piston rod 54cR moves upward, and the tensile test piece T is released from the holding arms 54b.

The operation of the chuck cylinder 54c is controlled by a second electromagnetic valve 85a. The second electromagnetic valve 85a includes a first port 85a1, a second port 85a2, a third port 85a3 and a fourth port 85a3. The second electromagnetic valve 85a is configured such that a first state in which the first port 85a1 and the third port 85a3 are connected and the second port 85a2 and the fourth port 85a4 are connected and a second state in which the first port 85a1 and the fourth port 85a4 are connected and the second port 85a2 and the third port 85a3 are connected are switched under control of the external controller 75. The first port 85a1, the second port 85a2, the third port 85a3 and the fourth port 85a4 of the second electromagnetic valve 85a are respectively connected to the oil tank 82, the discharge port 81a2 of the piston pump 81a, the rod side hydraulic chamber 54cB and the head side hydraulic chamber 54cA of the chuck cylinder 54c. In addition, a pilot check valve 86a is provided between the fourth port 85a4 of the second electromagnetic valve 85a and the head side hydraulic chamber 54cA of the chuck cylinder 54c. Furthermore, an accumulator 87a is located between the pilot check valve 86a and the head side hydraulic chamber 54cA of the chuck cylinder 54c.

When the second electromagnetic valve 85a is brought to the first state while the pump unit 81 draws the operating oil, the operating oil discharged from the pump unit 81 is sent to the pilot check valve 86a, and the inlet pressure of the pilot check valve 86a increases. Consequently, the pilot check valve 86a opens, and the operating oil is supplied to the head side hydraulic chamber 54cA of the chuck cylinder 54c. Furthermore, the operating oil is discharged from the rod side hydraulic chamber 54cB, and is returned to the oil tank 82. As a result, the piston rod 54cR of the chuck cylinder 51c is lowered, and the tensile test piece T (see FIG. 1) is held by the chuck device 54.

When the tensile test piece T is completely held, the inlet pressure and the outlet pressure of the pilot cheek valve 86a become substantially equal to each other, and thereby the pilot check valve 86a closes. At this time, the operating oil in the head side hydraulic chamber 54cA of the chuck cylinder 54c is pressurized by the inner pressure of the gas phase part of the accumulator 87a, and thereby the holding state of the tensile test piece T is maintained.

After the tensile test piece T is thus held, the pilot check valve 86a moves to the closed state. Therefore, back-flow of the operating oil does not occur even if the inlet pressure of the pilot check valve 86a becomes lower than the outlet pressure of the pilot check valve 86a, and therefore the pressure of the operating oil in the head side hydraulic chamber 54cA of the chuck cylinder 54c is not lowered. That is, once the tensile test piece T is held, the holding state of the tensile test piece T is not released unless the holding state is intentionally released.

When the second electromagnetic valve 85a is brought to the second state, the operating oil discharged from the pump unit 81 is supplied to the rod side hydraulic chamber 54cB of the chuck cylinder 51c, and the inner pressure of the rod side hydraulic chamber 54cB increases. As shown in FIG. 4, a pilot port of the pilot check valve 86a is connected to a pipe between the second electromagnetic valve 85a and the rod side hydraulic chamber 54cB, and the pilot check valve 86a opens when the inner pressure of the rod side hydraulic chamber 54cB exceeds a predetermined setting value. Therefore, when the second electromagnetic valve 85a is brought to the second state, the operating oil in the head side hydraulic chamber 54cA is returned to the oil tank 82, and the piston rod 54cR of the chuck cylinder 54c moves upward, and thereby the holding state of the tensile test piece T (see FIG. 1) is released.

As shown in FIG. 4, the chuck cylinder 65c is a double action hydraulic cylinder including a sleeve 65cS and a piston 65cP provided in the sleeve 65cS to be slidable. An inner space of the sleeve 65cS is divided by the piston 65cP into a head side hydraulic chamber 65cA and a rod side hydraulic chamber 65c8. The divided chambers are connected respectively to the hydraulic circuit. By supplying the operating oil to the head side hydraulic chamber 65cA and by discharging the operating oil from the rod side hydraulic chamber 65cB, the piston rod 65cR moves upward, and the holding arms 65b (see FIG. 2) hold the tensile test piece T. By discharging the operating oil from the head side hydraulic chamber 65cA and by supplying the operating oil to the rod side hydraulic chamber 65cB, the piston rod 65cR is lowered, and the tensile test piece T is released from the holding arms 65b.

The operation of the chuck cylinder 65c is controlled by a third electromagnetic valve 85b. The third electromagnetic valve 85b includes a first port 85b1, a second port 85b2, a third port 85b3 and a fourth port 85b3. The third electromagnetic valve 85b is configured such that a first state in which the first port 85b1 and the third port 85b3 are connected and the second port 85b2 and the fourth port 85b4 are connected and a second state in which the first port 85b1 and the fourth port 85b4 are connected and the second port 85b2 and the third port 85b3 are connected are switched under control of the external controller 75. The first port 85b1, the second port 85b2, the third port 85b3 and the fourth port 85h4 of the third electromagnetic valve 85b are respectively connected to the oil tank 82, the discharge port 81a2 of the piston pump 81a, the rod side hydraulic chamber 65cB and the head side hydraulic chamber 65cA of the chuck cylinder 65c. In addition, a pilot check valve 86b is provided between the fourth port 85b4 of the third electromagnetic valve 85b and the head side hydraulic chamber 65cA of the chuck cylinder 65c. Furthermore, an accumulator 87b is located between the pilot check valve 86b and the head side hydraulic chamber 65cA of the chuck cylinder 65c.

When the third electromagnetic valve 85b is brought to the first state while the pump unit 81 draws the operating oil, the operating oil discharged from the pump unit 81 is sent to the pilot check valve 86b, and the inlet pressure of the pilot check valve 86b increases. Consequently, the pilot check valve 86b opens, and the operating oil is supplied to the head side hydraulic chamber 65cA of the chuck cylinder 65c. Furthermore, the operating oil is discharged from the rod side hydraulic chamber 65cB, and is returned to the oil tank 82. As a result, the piston rod 65cR of the chuck cylinder 65c moves upward, and the tensile test piece T (see FIG. 1) is held by the chuck device 65.

When the tensile test piece T is completely held, the inlet pressure and the outlet pressure of the pilot check valve 86b become substantially equal to each other, and thereby the pilot check valve 86b closes. At this time, the operating oil in the head side hydraulic chamber 65cA of the chuck cylinder 65c is pressurized by the inner pressure of the gas phase part of the accumulator 87b, and thereby the holding state of the tensile test piece T is maintained.

After the tensile test piece T is thus held, the pilot check valve 86b moves to the closed state. Therefore, back-flow of the operating oil does not occur even if the inlet pressure of the pilot check valve 86b becomes lower than the outlet pressure of the pilot check valve 86b, and therefore the pressure of the operating oil in the head side hydraulic chamber 65cA of the chuck cylinder 65c is not lowered. That is, once the tensile test piece T is held, the holding state of the tensile test piece T is not released unless the holding state is intentionally released.

When the third electromagnetic valve 85b is brought to the second state, the operating oil discharged from the pump unit 81 is supplied to the rod side hydraulic chamber 65cB of the chuck cylinder 65c, and the inner pressure of the rod side hydraulic chamber 65cB increases. As shown in FIG. 4, a pilot port of the pilot check valve 86b is connected to a pipe between the third electromagnetic valve 85b and the rod side hydraulic chamber 65cB, and the pilot check valve 86b opens when the inner pressure of the rod side hydraulic chamber 65cB exceeds a predetermined setting value. Therefore, when the third electromagnetic valve 85b is brought to the second state, the operating oil in the head side hydraulic chamber 65cA is returned to the oil tank 82, and the piston rod 65cR of the chuck cylinder 65c is lowered, and thereby the holding state of the tensile test piece T (see FIG. 1) is released.

The hydraulic control system 80 of the universal testing machine 1 according to the embodiment of the invention includes reducing modular valves 84a and 84b which are respectively located between the discharge port 81a2 of the piston pump 81a and the second electromagnetic valve 85a and between the discharge port 81a2 of the piston pump 81a and the third electromagnetic valve 85h. The reducing modular valve 84a has an inlet 84a1, an outlet 84a2 and a relief port 84a3. The inlet 84a1, the outlet 84a2 and the relief port 84a3 are respectively connected to the discharge port 81a2 of the piston pump 81a, the second port 85a2 of the second electromagnetic valve 85a and the oil tank 82. Similarly, the reducing modular valve 84b has an inlet 84b1, an outlet 84b2 and a relief port 84b3. The inlet 84b1, the outlet 84b2 and the relief port 84b3 are respectively connected to the discharge port 81a2 of the piston pump 81a, the second port 85b2 of the second electromagnetic valve 85b and the oil tank 82. The reducing modular valves 84a and 84b are valves configured to reduce the pressure of the outlets 84a2 and 84b2 to be lower than or equal to a predetermined setting pressure by releasing part of the operating oil introduced from the inlets 84a1 and 84b1 through the relief ports 84a3 and 84b3. If the pressure of the inlet 84a1 and 84b1 is larger than or equal to the predetermined setting pressure, the pressure of the outlet 84a2 and 84b2 is kept at the predetermined setting pressure.

As described above, the reducing modular valves 84a and 84b return the part of the operating oil supplied from the piston pump 81a to the oil tank 82. Therefore, the flow amount of the operating oil sent to the main cylinder unit 30 when the first electromagnetic valve 83 is switched to the third state and thereby lifts up the moving plate 50 becomes smaller than the flow amount of the operating oil sent out from the discharge port 81a2 of the piston pump 81a.

The piston pump 81a supplies the operating oil whose flow amount is proportional to the rotation speed of the servo motor 81b, by driving the piston by the servo motor 81b to reciprocate. In such a piston pump 81a, when the cycle number decreases, pulsation is caused in the operating oil, and thereby control of the flow amount of the operating oil becomes difficult. On the other hand, when the tensile test or the compression test is performed by the universal testing machine 1, the moving plate 50 needs to be driven at a low speed because it is necessary to apply a substantial static load to the test piece.

In this embodiment, the servo motor 81b of the pump unit 81 is controlled to be driven at a constant rotation speed so that the flow amount of the operating oil required to prevent occurrence of the pulsation which would affect the test can be secured. On the other hand, as described above, by increasing the flow amount of the operating oil returned from the reducing modular valves 84a and 84b to the oil tank 82, the flow amount of the operating oil supplied to the main cylinder unit 30 can be reduced, and thereby the moving speed of the moving plate 50 can be decreased to a sufficiently low speed t'e.g., 0.1 mm/s or less) necessary for the static load test. Therefore, the universal testing machine 1 according to the embodiment of the invention is able to drive the moving plate 50 at a low speed and to apply the static load to the tensile test piece T or the compression test piece P, while preventing occurrence of the pulsation.

Figure 5:
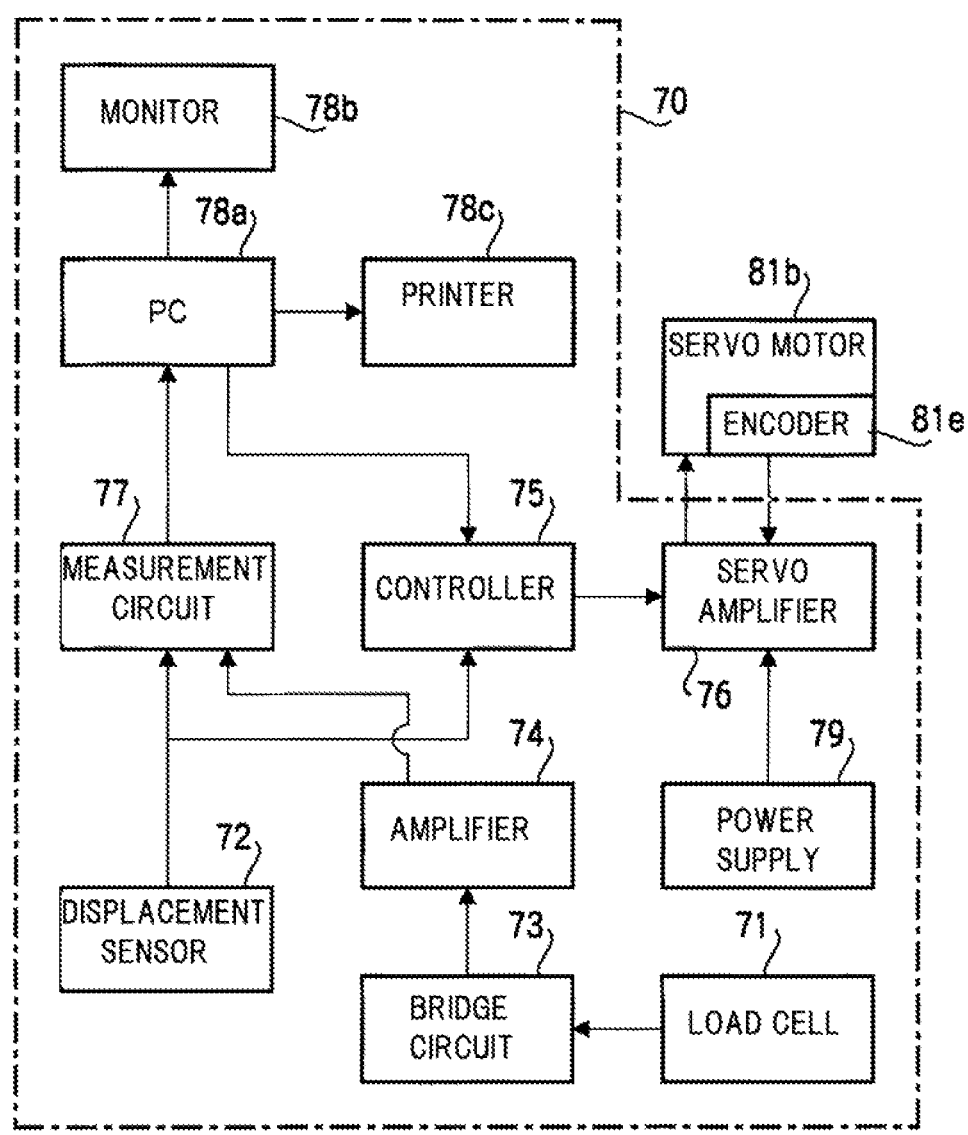
FIG. 5 is a block diagram generally illustrating a control and measurement unit of the universal testing machine according to the embodiment of the invention.

Next, the control and measurement of the universal testing machine 1 according to the embodiment of the invention are explained. FIG. 5 is a block diagram generally illustrating the control and measurement unit 70 which performs the driving control and the measurement process of the universal testing machine 1. The control and measurement unit 70 includes the load cell 71, the displacement sensor 72, a bridge circuit 73, an amplifier 74, the controller 75, a servo amplifier 76, a measurement circuit 77, a PC 78a, a monitor 78b, a printer 78c and a power supply 79.

The servo amplifier 76 generates a driving current for driving the servo motor 81b from power supplied from the power supply 70 based on a target speed signal sent from the controller 75, and supplies the driving current to the servo motor 81b. An encoder 81e for measuring the rotation speed of the servo motor 81b is provided on a drive shaft of the servo motor 81b. The servo amplifier 76 executes the feedback control in which the power (e.g., a pulse width of the driving current in the case of the pulse width modulation) to be supplied to the servo motor 81b is adjusted based on the rotation speed of the drive shaft of the servo motor 81b. With this configuration, the servo motor 81b is controlled so that the rotation speed of the drive shaft of the servo motor 81b becomes equal to the target speed.

An output of the load, cell 71 which measures the load applied to the test piece is input to the measurement circuit 77 via the bridge circuit 73 and the amplifier 74. Similarly, an output of the displacement sensor 72 for measuring the displacement of the test piece is input to the measurement circuit 77. The measurement circuit 77 executes A-D conversion for the analog signals from the load cell 71 and the displacement sensor 72, and transmits the converted signals to the PC 78a.

The PC 78a plots a graph based on the load and displacement transmitted from the measurement circuit 77, and displays it on the monitor 78b. For example, the PC 78a calculates the stress applied to the test piece from the measurement value of the load and the sectional area of the test piece which has been measured in advance, and calculates the distortion of the test piece from the measurement value of the displacement and the size (actually, the distance between the chucks) of the test piece in the applying direction of the load. Then, the PC 78a displays the plot of the stress-distortion curve. The PC 78a is also able to print out the plotted graph By operating the PC 78a, an operator of the universal testing machine 1 transmits an indication value of the moving speed of the moving plate 50 to the controller 75. Based on the indication value of the moving speed and the displacement amount sent from the displacement sensor 72, the controller 75 calculates the target speed signal to be sent to the servo amplifier 76, and transmits the target speed signal to the servo amplifier 76.

Figure 6:
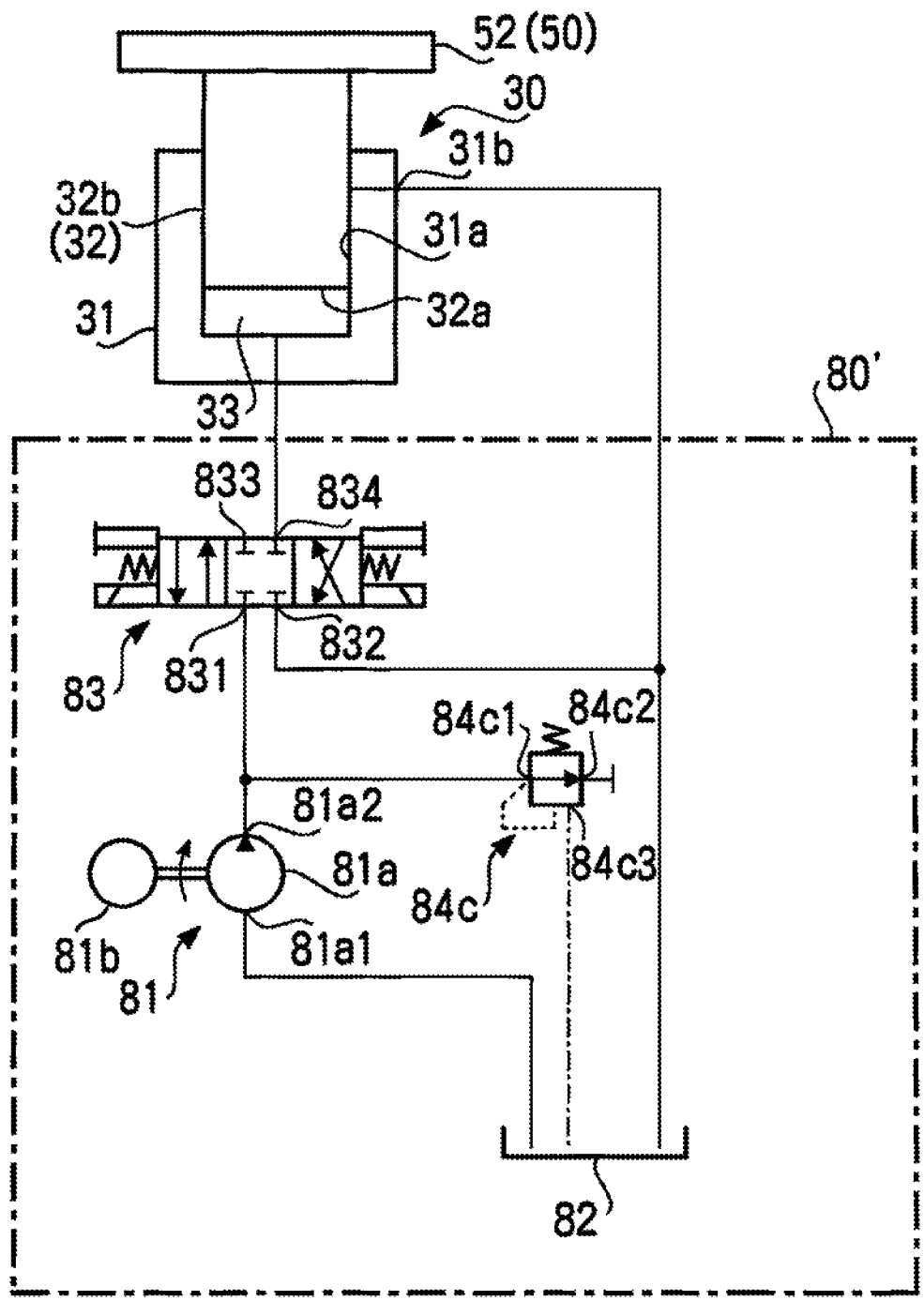
FIG. 6 is a diagram generally illustrating a hydraulic circuit according to another embodiment of the invention.

In the above explained embodiment, the main cylinder unit and the pair of chuck cylinders are driven by the hydraulic pressure supplied by the pump unit. However, the present invention can also be applied to a hydraulic control system having a simpler configuration. FIG. 6 is a diagram generally illustrating a hydraulic circuit of a hydraulic control system 80' according to another embodiment of the invention. In FIG. 6, to elements which are substantially the same as those of the above described embodiment, the same reference numbers are assigned, and explanations thereof are omitted.

In this embodiment, to a branch tube branched from the tube connecting the discharge port 81a2 of the piston pump 81a and the first electromagnetic valve 83, a reducing modular valve 84c is directly connected. An outlet 84c2 of the reducing modular valve 84c is closed, and a relief port 84c3 is connected to the oil tank 82. The reducing modular valve 84c is configured to return the operating oil to the oil tank 82 via the relief port 84c3 while maintaining the input side pressure so that the discharge amount of the piston pump 81a is secured to the extent that pulsation is not caused when the pump unit 81 drives the cylinder unit 30. For example, when $D_{min}$, (L/min) denotes the minimum discharge amount of the piston pump 81a required for not causing the pulsation, the reducing modular valve 84c is set to return the amount larger than or equal to $D_{min}$ (L/min) from the relief port 84c3 to the oil tank 82 during driving of the cylinder unit 30.

The foregoing is the explanation of the illustrative embodiments. It is understood that not all of the above described features are necessarily provided in another embodiment, and another embodiment may additionally or alternatively include another feature. For example, in the above described embodiment, a hydraulic cylinder is used as a hydraulic actuator. However, the type of the actuator is not limited to the above described example. For example, a hydraulic system and a universal testing machine including a well-known actuator, such as an oil motor, are also included in the scope of the present invention. The hydraulic pump is not limited to the piston pump, the present invention can effectively be applied to the case where a well-know pump causing an undesirable phenomenon, such as pulsation, at a low driving speed at which the discharge amount is low is used. The driving source for the hydraulic pump is not limited to the servo motor, and another type of driving source capable of continuously adjusting the rotation speed may be used.

What is claimed is:

1. An hydraulic system, comprising:
an oil tank storing operating oil;
a main hydraulic actuator;
a second hydraulic actuator which operates at a hydraulic pressure lower than or equal to a predetermined pressure;
a hydraulic pump which draws the operating oil from the oil tank and supplies the operating oil to the main and second hydraulic actuators;
a main tube which sends the operating oil from the hydraulic pump to the main hydraulic actuator;
a second tube which sends the operating oil to the second hydraulic actuator; and
an operating oil separating unit which is located at a midway point of the main tube and which separates a part of the operating oil supplied from the hydraulic pump to return the part of the operating oil to the oil tank,
the operating oil separating unit comprising:
a branch tube which branches out from the main tube; and
a reducing valve having an inlet port connected to the branch tube, an outlet port connected to the second tube, and a relief port connected to the oil tank,
wherein:
the reducing valve reduces a pressure of the outlet port to be lower than or equal to a predetermined pressure by separating the part of the operating oil introduced from the inlet port to proceed from the relief port to the oil tank; and
a flow amount of the operating oil separated by the reducing valve is set to a value which the hydraulic pump should maintain to reduce pulsation to be lower than or equal to a desired level.

2. The hydraulic system according to claim 1, wherein a discharge pressure of the hydraulic pump is supplied to the main hydraulic actuator without being substantially reduced.

3. The hydraulic system according to claim 2, wherein the main hydraulic actuator is connected to the hydraulic pump without intervention by a flow control valve for controlling continuously a flow amount.

4. The hydraulic system according to claim 3, wherein the main hydraulic actuator is connected to the hydraulic pump without intervention by a throttle valve.

5. The hydraulic system according to claim 1, further comprising a motor which drives the hydraulic pump.

6. The hydraulic system according to claim 5, wherein the motor is a servo motor.

7. The hydraulic system according to claim 1, wherein the hydraulic pump is a piston pump.

8. A universal testing machine, comprising a hydraulic system according to claim 1.

9. A universal testing machine, comprising:
a fixed plate;
a moving plate capable of moving with respect to the fixed plate; and
a hydraulic system which moves the moving plate so as to apply a static load to a test piece held between the fixed plate and the moving plate,
the hydraulic system comprising:
an oil tank storing operating oil;
a main hydraulic cylinder having a piston and a sleeve, one of which is fixed to the moving plate, the main hydraulic cylinder being able to operate at a hydraulic pressure higher than a predetermined pressure;
a hydraulic pump which draws the operating oil from the oil tank and supplies the operating oil to the main hydraulic cylinder;
a servo motor which drives the hydraulic pump;
an operating oil separating unit which is located between the hydraulic pump and the main hydraulic cylinder and which separates a part of the operating oil supplied from the hydraulic pump to return the part of the operating oil to the oil tank; and
a chuck unit having a holding arm which holds the test piece and a chuck hydraulic cylinder which drives the holding arm by the operating oil supplied from the hydraulic pump,
wherein:
the operating oil separating unit is a reducing valve having an inlet port connected to the hydraulic pump, an outlet port connected to the chuck cylinder, and a relief port connected to the oil tank;
the reducing valve reduces a pressure of the outlet port actuating the chuck hydraulic cylinder to be lower than or equal to a predetermined pressure by separating the part of the operating oil introduced from the inlet port to proceed from the relief port to the oil tank; and
a flow amount of the operating oil separated by the redwing valve is set to a value which the hydraulic pump should maintain to reduce pulsation to be lower than or equal to a desired level.

10. The universal testing machine according to claim 9, wherein the chuck unit holds the test piece when the operating oil is supplied to one of hydraulic chambers of the chuck hydraulic cylinder and a piston is moved,
the universal testing machine further comprising:
a check valve which is located between the one of the hydraulic chambers of the chuck hydraulic cylinder and the hydraulic pump and which prevents back-flow of the operating oil from the one of the hydraulic chambers to the hydraulic pump while the test piece is held.

11. The universal testing machine according to claim 10, further comprising a switch valve which is located between the hydraulic pump and the chuck hydraulic cylinder and which switches between a state of sending the operating oil supplied from the hydraulic pump to the one of the hydraulic chambers and a state of sending the operating oil supplied from the hydraulic pump to the other of the other hydraulic chambers,
wherein;
the chuck unit releases a holding state of the test piece when the operating oil is supplied to the other of the hydraulic chambers of the chuck hydraulic cylinder and the piston is moved; and
the check valve is a pilot check valve whose pilot port is connected to the other of the hydraulic chambers, and when the operating oil is supplied to the other of the hydraulic chambers, the pilot check valve opens and the operating oil is discharged from the one of the hydraulic chambers.

12. The universal testing machine according to claim 10, further comprising an accumulator arranged between the check valve and the one of the hydraulic chambers.

13. A hydraulic system, comprising:
an oil tank storing operating oil;
a first actuator;
a hydraulic pump which draws the operating oil from the oil tank and supplies the oil tank to the first hydraulic actuator;
a main tube which sends the operating oil from the hydraulic pump to the first actuator; and
an operating oil separating unit which is located at a midway point of the main tube and which separates a part of the operating oil supplied from the hydraulic pump to return the part of the operating oil to the oil tank;
wherein:
the hydraulic pump comprises a servo motor, and is configured to be able to control a discharge amount of the operating oil by controlling a rotation speed of the servo motor; and
a flow amount of the operating oil separated by the operating oil separating unit is set to a value which the hydraulic pump should maintain to reduce pulsation to be lower than or equal to a desired level.

14. The hydraulic system according to claim 13, wherein the servo motor is controlled to rotate at a rotation speed larger than or equal to a predetermined rotation speed so as to secure a certain flow amount of the operating oil required to suppress the pulsation to be lower than or equal to the desired level.

15. The hydraulic system according to claim 13, wherein a flow amount of the operating oil separated by the he operating oil separating unit is set such that a flow amount of the operating oil supplied to the first hydraulic actuator reduces and thereby a moving speed of a moving plate of the first hydraulic actuator becomes a speed required for a static load test.

16. The hydraulic system according to claim 15, wherein the moving speed of the moving plate of the first hydraulic actuator is lower than or equal to 0.1 mm/s.

17. A universal testing machine, comprising:
a fixed plate;
a moving plate capable of moving with respect to the fixed plate; and
a hydraulic system which moves the moving plate so as to apply a static load to a test piece held between the fixed plate and the moving plate,
the hydraulic system comprising:
an oil tank storing operating oil;
a main hydraulic cylinder having a piston and a sleeve, one of which is fixed to the moving plate, the main hydraulic cylinder being able to operate at a hydraulic pressure higher than a predetermined pressure;
a hydraulic pump which draws the operating oil from the oil tank and supplies the operating oil to the main hydraulic cylinder; and
an operating oil separating unit which is located between the hydraulic pump and the main hydraulic cylinder and which separates a part of the operating oil supplied from the hydraulic pump to return the part of the operating oil to the oil tank,
wherein:
the hydraulic pump comprises a servo motor, and is configured to be able to control a discharge amount of the operating oil by controlling a rotation speed of the servo motor; and
a flow amount of the operating oil separated by the operating oil separating unit is set to a value which the hydraulic pump should maintain to reduce pulsation to be lower than or equal to a desired level.

18. The universal testing machine according to claim 17, wherein the servo motor is controlled to rotate at a rotation speed larger than or equal to a predetermined rotation speed so as to secure a certain flow amount of the operating oil required to suppress the pulsation to be lower than or equal to the desired level.

19. The universal testing machine according to claim 17, wherein a flow amount of the operating oil separated by the he operating oil separating unit is set such that a flow amount of the operating oil supplied to the first hydraulic actuator reduces and thereby a moving speed of a moving plate of the first hydraulic actuator becomes a speed required for a static load test.

20. The universal testing machine according to claim 19, wherein the moving speed of the moving plate of the first hydraulic actuator is lower than or equal to 0.1 mm/s.

* * * * *

UNITED STATES PATENT AND TRADEMARK OFFICE
CERTIFICATE OF CORRECTION

Page 1 of 2

PATENT NO.         : 8,596,058 B2
APPLICATION NO.    : 13/290481
DATED              : December 3, 2013
INVENTOR(S)        : Sigeru Matsumoto et al.

It is certified that error appears in the above-identified patent and that said Letters Patent is hereby corrected as shown below:

In the Claims

Column 14, lines 27-67, please correct claim 9 to read as follows:

9. A universal testing machine, comprising: a fixed plate; a moving plate capable of moving with respect to the fixed plate; and a hydraulic system which moves the moving plate so as to apply a static load to a test piece held between the fixed plate and the moving plate, the hydraulic system comprising: an oil tank storing operating oil; a main hydraulic cylinder having a piston and a sleeve, one of which is fixed to the moving plate, the main hydraulic cylinder being able to operate at a hydraulic pressure higher than a predetermined pressure; a hydraulic pump which draws the operating oil from the oil tank and supplies the operating oil to the main hydraulic cylinder; a servo motor which drives the hydraulic pump; an operating oil separating unit which is located between the hydraulic pump and the main hydraulic cylinder and which separates a part of the operating oil supplied from the hydraulic pump to return the part of the operating oil to the oil tank; and a chuck unit having a holding arm which holds the test piece and a chuck hydraulic cylinder which drives the holding arm by the operating oil supplied from the hydraulic pump, wherein: the operating oil separating unit is a reducing valve having an inlet port connected to the hydraulic pump, an outlet port connected to the chuck cylinder, and a relief port connected to the oil tank; the reducing valve reduces a pressure of the outlet port actuating the chuck hydraulic cylinder to be lower than or equal to a predetermined pressure by separating the part of the operating oil introduced from the inlet port to proceed from the relief port to the oil tank; and a flow amount of the operating oil separated by the ~~redwing~~ reducing valve is set to a value which the hydraulic pump should maintain to reduce pulsation to be lower than or equal to a desired level.

Column 16, lines 1-7, please correct claim 15 to read as follows:

15. The hydraulic system according to claim 13, wherein a flow amount of the operating oil separated by the ~~he~~ operating oil separating unit is set such that a flow amount of the operating oil Signed and Sealed this
Twenty-second Day of July, 2014

Michelle K. Lee
*Deputy Director of the United States Patent and Trademark Office* supplied to the first hydraulic actuator reduces and thereby a moving speed of a moving plate of the first hydraulic actuator becomes a speed required for a static load test.

Column 16, lines 48-54, please correct claim 19 to read as follows:

19. The universal testing machine according to claim 17, wherein a flow amount of the operating oil separated by the ~~he~~ operating oil separating unit is set such that a flow amount of the operating oil supplied to the first hydraulic actuator reduces and thereby a moving speed of a moving plate of the first hydraulic actuator becomes a speed required for a static load test.